US006623952B1

(12) United States Patent
Sandstrom et al.

(10) Patent No.: US 6,623,952 B1
(45) Date of Patent: Sep. 23, 2003

(54) SPUMAVIRUS ISOLATED FROM HUMANS

(75) Inventors: Paul A. Sandstrom, Kanata (CA); Thomas M. Folks, Snellville, GA (US); Walid M. Heneine, Atlanta, GA (US); William M. Switzer, Stone Mountain, GA (US); Jennifer Brown, Sacramento, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/830,616

(22) PCT Filed: Oct. 27, 1999

(86) PCT No.: PCT/US99/25171
§ 371 (c)(1),
(2), (4) Date: Sep. 5, 2001

(87) PCT Pub. No.: WO00/24876
PCT Pub. Date: May 4, 2000

Related U.S. Application Data

(60) Provisional application No. 60/105,811, filed on Oct. 27, 1998.

(51) Int. Cl.[7] .................................................. C12N 7/00

(52) U.S. Cl. .................. 435/235.1; 435/239; 435/320.1

(58) Field of Search ............................. 435/235.1, 239, 435/320.1

(56) References Cited

U.S. PATENT DOCUMENTS

| 5,108,920 A | 4/1992 | Ng et al. |
| 5,459,056 A | 10/1995 | Powell et al. |
| 5,597,896 A | 1/1997 | Montagnier et al. |
| 5,646,032 A | 7/1997 | ter Meulen et al. |
| 5,882,912 A | 3/1999 | Sandstrom et al. |

FOREIGN PATENT DOCUMENTS

| DE | 43 18387 | 12/1994 |
| WO | WO 98/35024 | 8/1998 |
| WO | WO 00/77177 | 12/2000 |

OTHER PUBLICATIONS

Heneine, Nature Medicine, 1998 4(4) p. 403–407.*
Schweitzer et al. 1997, J of Virology 71: 4821–4824.*
EMBL Database AF049084 and AF049084.*
Anonymous Survey for Simian Immunodeficiency Virus (SIV) Seropositivity in SIV—Laboratory Researchers—United States, 1992. MMWR Morb. Mort. Wkly Rep. 41(43):814–815 (Oct. 30, 1997).
Callahan et al. Persistent Zoonotic Infection of a Human with Simian Foamy Virus in the Absence of an Intact orf –2 Accessory Gene. J. of Virol. 73(11):9619–9624 (Nov. 1999).
Cordonnier et al. Isolation of Novel Human Endogenous Retrovirus–Like Elements with Foamy Virus–Related pol Sequence. J. of Virol. 69(9):5890–5897 (Sep. 1995).
Giron et al. Human Foamy Virus Polypeptides: Identification of env and bel Gene Products. J. of Virol. 67(6):3596–3600 (Jun. 1993).
Hahn et al. Reactivity of primate sera to foamy virus Gag and Bet proteins. J. of Gen. Virol. 75:2635–2644 (1994).
Heneine et al. Detection of Reverse Transcriptase by a Highly Sensitive Assay in Sera from Persons Infected with Human Immunodeficiency Virus Type–1. J. Infect. Dis. 171:1210–1216 (May 1995).
Heneine et al. Absence of Evidence for Human Spumaretrovirus Sequences in Patients with Graves'Disease [letter]. J. Acq. Immune Defic. Synd. & Human Retrov. 9:99–101 (1995).
Herchenroder et al. Isolation, Cloning, and Sequencing of Simian Foamy Viruses from Chimpanzees (SFVcpz): High Homology to Human Foamy Virus (HFV). Virology. 201:187–199 (1994).
Hirata et al. Transduction of Hematopoietic Cells by Foamy Virus Vectors. Blood. 88(9):3654–3661 (Nov. 1, 1996).
Hooks et al. The Foamy Viruses. Bacteriol. Rev. 39(3):169–185 (Sep. 1975).
Khabbaz et al. Simian immunodeficiency virus needlestick accident in a laboratory worker. Lancet 340:271–273 (1992).
Khabbaz et al. Brief Report: Infection of a Laboratory Worker with Simian Immunodeficiency Virus. N. Eng. J. Med. 330:172–177 (1994).
Lairmore et al. Perspectives in Disease Prevention and Health Promotion Guidelines to Prevent Simian Immunodeficiency Virus Infection in Laboratory Workers and Animal Handlers. MMWR Morb. Mort. Wkly Rep. 37(45):693–694, 699–704 (Nov. 18, 1988).
Loh. Spumaviruses. The Retroviridae. 2:361–397 (1993).
Mahnke et al. Specific enzyme–linked immunosorbent assay for the detection of antibodies to the human spumavirus. J. Virol. Meth. 29:13–22 (1990).
McClure et al. Isolation of a New Foamy Retrovirus from Orangutans. J. of Virol. 68(11):7124–7130 (Nov. 1994).
Mergia et al. Cell tropism of the simian foamy virus type 1 (SFV–1). J. Med. Primatol., 25:2–7 (Jul. 21, 1995).

(List continued on next page.)

Primary Examiner—James Housel
Assistant Examiner—Myron G. Hill
(74) Attorney, Agent, or Firm—Needle & Rosenberg, P.C.

(57) ABSTRACT

The present invention comprises a spumavirus isolated from a human. More specifically, the spumavirus of the present invention was isolated from a human who had exposure to nonhuman primates. Importantly, the spumavirus of the present invention or antibodies to the spumavirus can be used to detect the presence of spumavirus or antibodies in body fluids, for pathogenicity studies of related viruses, and as a vector for gene therapies. The spumavirus of the invention can also be used for treatment of conditions in humans due to the presence of rapidly dividing cells and for recombinant live virus vaccination.

3 Claims, 6 Drawing Sheets

OTHER PUBLICATIONS

Renne et al. Genomic Organization and Expression of Simian Foamy Virus Type 3 (SFV-3). *Virology* 186:597–608 (1992).

Russell et al. Foamy Virus Vectors. *J. of Virol.* 70(1):217–222 (Jan. 1996).

Schweizer et al. Phylogenetic Analysis of Primate Foamy Viruses by Comparison of pol Sequences. *Virology* 207:577–582 (1995).

Weissenberger et al. Identification and Characterization of the Bel 3 Protein of Human Foamy Virus. *AIDS Res. Hum. Retrov.* 10(5):595–600 (1994).

EMBL Database; EMVRL:AF049085; Accession No. AF049085 (Aug. 4, 1998).

EMBL Database; EMVRL:AF049084; Accession No. AF049084 (Aug. 4, 1998).

Heneine et al. "Identification of a human population infected with simian foamy viruses" *Nature Medicine* 4(4):403–7 (Apr. 1998).

Schweizer et al. "Simian foamy virus isolated from an accidentally infected human individual" *J. Virol.* 71(6):4821–4824 (Jun. 1997).

Ali et al. "No evidence of antibody to human foamy virus in widespread human populations" *AIDS Re and Human Retroviruses* 12(15):1473–1483 (1996).

DHHS Docket No. 96M–0311, Draft Public Health Service (PHS) Guideline on Infectious Disease Issues in Xenotransplantation. *Federal Register* 61:185 (Sep. 23, 1996).

Chapman et al. "Xenotransplantation and xenogeneic infections" *New Eng. J. Med.* 333:1498–1501 (1995).

Heneine et al. "Absence of evidence of human spumaretrovirus sequences in patients with Graves'disease [letter]" *J. Acquir. Immune Defic. Syndr. & Human Retrovirol.* 9:99–101 (1995).

Schweizer et al. "Markers of foamy virus infections in monkeys, apes, and accidentally infected humans: appropriate testing fails to confirm suspected foamy virus prevalence in humans" *AIDS Re & Hum. Retroviruses* 11(1):161–70 (1995).

Heneine et al. "Lack of evidence for infection with known human and animal retroviruses in patients with chronic fatigue syndrome" *Clin. Infect. Dis.* 18:s121–5 (1994).

Schweizer et al. "Absence of foamy virus DNA in Graves'disease" *AIDS Re & Hum. Retroviruses.* 10:601–5 (1994).

Simonsen et al. "Absence of evidence for infection with the human spumaretrovirus in an outbreak of Meniere–like vertiginous illness in Wyoming. USA [letter] "*Acta Oto-–Laryngologica* 114:223–4 (1994).

Neumann–Haefelin et al. "Foamy viruses" *Intervirology* 35:196–207 (1993).

Neumann–Haefelin et al. "Nonhuman Primate Spumavirus Infections Among Persons with Occupational Exposure" *Morbidity and Mortality Weekly Report* 46(6): 129–131.

\* cited by examiner

SFV Western Blot Profiles

SIMIAN FOAMY VIRUS PERCENT NUCLEOTIDE IDENTITY

| | CASE A | CASE B | CASE C | CASE D | SFV3 AGM | SFV10 BAB | SFV MAC | HFV | SFV6 CPZ | SFV PYG | SFV8 SPM |
|---|---|---|---|---|---|---|---|---|---|---|---|
| CASE A | – | 82.6 | 82.1 | 81.6 | 87.5 | 82.1 | 77.4 | 68.7 | 66.6 | 67.2 | 66.4 |
| CASE B | – | – | 95.5 | 85.0 | 81.7 | 96.4 | 76.2 | 68.3 | 66.4 | 68.9 | 62.3 |
| CASE C | – | – | – | 84.6 | 82.1 | 97.2 | 76.9 | 67.5 | 66.5 | 69.3 | 62.3 |
| CASE D | – | – | – | – | 80.5 | 85.6 | 76.9 | 69.4 | 67.3 | 68.3 | 64.0 |

Figure 6

SPUMAVIRUS ISOLATED FROM HUMANS

This application is a National Stage Entry of PCT/US99/25171, filed Oct. 27, 1999, which claims priority to Ser. No. 60/105,811, filed Oct. 27, 1998.

This invention was made by the Centers for Disease Control and Prevention, an agency of the United States Government.

TECHNICAL FIELD

The present invention relates to a novel retrovirus, a spumavirus, that has been isolated from humans. More particularly, the novel spumavirus may be used as a vector for gene therapy. The novel spumavirus may also be used as a recombinant live virus vaccine.

BACKGROUND OF THE INVENTION

Spumavirus, also known as foamy virus for the characteristics of vacuolization the virus induces in cell culture, belongs to a distinct group of retroviruses. The simian foamy viruses (SFVs) include isolates from Old World and New World monkeys and are classified into 10 different serotypes based on serological cross-reactivities. Virus appears to persist in the host for a long period of time in a latent form and can exist in the presence of neutralizing antibody.

Currently the most studied retrovirus, Human Immunodeficiency Virus, is believed to be derived from nonhuman primate transmission into humans at some past time. Concerns about the risk of transmission of retroviruses from non-human primates to humans working in research laboratories were heightened in the early 1990's when two persons developed antibodies to SIV (Simian Immunodeficiency Virus) following work-related exposures, one of whom had clear evidence of persistent viral infection. (See CDC Anonymous survey for simian inmmunodeficiency virus (SIV) seropositivity in SIV laboratory researchers—United States, 1992. MMWR Morb. Mort. Wkly. Rep. 1992; 41: 814–5; Khabbaz R. F., et al. Brief report: infection of a laboratory worker with simian immunodeficiency virus. New Eng. J. Med. 1994; 330: 172–7; Khabbaz R. F., et al. Simian immunodeficiency virus needlestick accident in a laboratory worker. Lancet 1992; 340: 271–3: and CDC. Guideline to prevent simian immunodeficiency virus infection in laboratory workers and animal handlers. MMWR 1988; 37: 693–704.) In addition to SIV, nonhuman primate species used in biomedical research are commonly infected with SFV (simian foamy virus), STLV (simian t-cell lymphotrophic virus), and/or type D retroviruses. All of these retroviruses cause lifelong infections in nonhuman primates, and some are known to be transmissible through sexual contact, blood, or breast feeding. Natural SFV infections in non-human primates have not been definitively associated with disease. In non-human primates, infection with the other retroviruses may result in a clinical spectrum ranging from asymptomatic infection to life threatening immunodeficiency syndromes or lymphoproliferative disorders. The transmission routes of SFVs among non-human primates remain undefined, but the prevalence of seroreactivity is high among captive adult non-human primates.

Studies of the prevalence of spumavirus infection of humans are limited and the findings are not definitive. Though there is some evidence of human infection with SFV (antibodies and positive PCR results), such occurrence has been reported in only two persons, both of whom had occupational risks for infection. Associated disease was not reported in either. (See Schweizer M., et al. Absence of foamy virus DNA in Graves' disease. AIDS Res. & Human Retrov. 1994; 10: 601–5; Neumann-Haefelin D., et al., Foamy viruses. Intervirology 1993; 35: 196–207; and Schweizer M., et al., Markers of foamy virus infections in monkeys, apes, and accidentally infected humans: appropriate testing fails to confirm suspected foamy virus prevalence in humans. AIDS Res. & Human Retrov. 1995; 11: 161–70.)

Other inconclusive evidence was seen in early studies which described a relatively high rate of seroreactivity to antibodies to spumaviruses among human populations not known to be exposed to non-human primates. In some instances seroreactivity was suggestively linked to human disease, including disorders of the central nervous system, thyroid disease, and Chronic Fatigue Syndrome. In most instances these studies lacked definitive evidence of human infection and were not subsequently confirmed. (See Heneine, W., et al., Absence of evidence for human spumaretrovirus sequences in patients with Graves' disease [letter]. J. Acq. Immune Defic. Synd. & Human Retrov. 1995; 9: 99–101; Simonsen, L., et al. Absence of evidence for infection with the human spumaretrovirus in an outbreak of Meniere-like vertiginous illness in Wyoming, USA [letter]. Acta Oto-Laryngologica 1994; 114: 223–4; and Heneine, W., et al., Lack of evidence for infection with known human and animal retroviruses in patients with chronic fatigue syndrome. Clin. Infect. Dis. 1994; 18: S121–5).

Recent publications indicate that earlier serological tests showing human spumavirus antibodies in the human population were incorrect. Immunological investigation of a previously reported human spumavirus revealed that it shared common antigens in complement fixation, immunofluorescence and neutralization assays with the chimpanzee foamy virus, SFV-6. Furthermore, failure to detect serological evidence of HFV infection in people from a wide geographical area suggested that this virus isolate was a variant of SFV-6, particularly since sera from chimpanzees naturally infected with SFV-6 neutralized both viruses. In a survey for prevalence of human foamy virus in more than 5000 human sera, collected from geographically diverse populations, none of the serum samples were confirmed as positive. Taken together with sequence analysis endorsing the phylogenetic closeness of the purported human spumavirus to SFV-6/7, these data strongly suggest that human foamy virus is not naturally found in the human population. (See Ali, M. et al., "No Evidence of Antibody to Human Foamy Virus in Widespread Human Populations," AIDS Research and Human Retroviruses, Vol. 12, No. 15, 1996.)

Recent concern that xenotransplantation, the use of living tissues from nonhuman species in humans for medical purposes, may introduce new infections into the human community has increased the importance of defining the ability of simian retroviruses to infect and/or cause disease in humans (See Chapman, L. E., et al. Xenotransplantation and xenogeneic infections. New Engl. J. Med. 1995; 333: 1498–1501; DHHS. Docket No. 96M-0311. Draft Public Health Service (PHS) Guideline on Infectious Disease Issues in Xenotransplantation. Federal Register Vol.61, No. 185. Sep. 23, 1996.). The primary animal species considered as donors for xenografts are baboons and pigs. Thus, what is needed are compositions and methods for detecting viruses that may be transmitted from the nonhuman organ donors to the recipient human. Additionally, information regarding these transmissible agents may provide valuable information about the organ donors' cellular receptors that may be important for transplantation success.

Gene therapies have long looked for a good vector that can transport the foreign gene of choice into human cells.

The lack of any known disease associated with the virus of the present invention makes the present invention an ideal candidate for gene therapy regimens. Thus, compositions and methods for gene therapy are needed that use a vector capable of carrying a significant amount of foreign DNA that will enter the host organism and not cause disease.

Compositions and methods for vaccination using recombinant live retroviruses are also needed. A live virus, that causes no illness in humans, and that has genes of antigens of choice incorporated into its genome, would provide for an excellent vaccination tool. The retrovirus would reproduce in the human host and expose the immune system to antigens so that an immune response can be initiated.

Targeted attack on reproducing cells is a goal of cancer treatment. What is needed are compositions and methods for cancer treatment that are specific for dividing cells that do not cause systemic damage to the cancer patient. A virus that could infect and kill dividing cells, without killing other cells of the host would provide a solution for cancer treatment.

SUMMARY OF THE INVENTION

The present invention is directed to compositions and methods comprising a novel spumavirus or foamy virus, known as SFVHu-3. The present invention comprises a spumavirus isolate of human origin that has been definitively isolated from a human with no disease. The novel spumavirus of the present invention has been maintained through tissue culture cells where it causes the characteristic vacuolation of the cells that is known for foamy viruses.

The novel spumavirus of the present invention has utility as a reagent for the immunological screening of the human population for the prevalence of such viruses in the population. The novel spumavirus of the present invention can also serve as a vector in gene therapy because the virus appears to cause no disease in humans and is not transmitted to other humans. Additionally, the novel spumavirus of the present invention can be used as a reagent in pathogenicity studies of these and related viruses. Moreover, the sequences of the novel spumavirus of the present invention can be used as probes to detect virus in biological samples. Vectors include, but are not limited to, procaryotic, eucaryotic and viral vectors. The foamy virus of the present invention can also be used as a live recombinant virus vaccine. Additionally, the spumavirus of the present invention can be used as a replicating viral system to kill live dividing cells, either in vitro or in vivo.

The spumaviruses or foamy viruses are by far the least well characterized of the retroviruses. They have been isolated as agents that cause vacuolation ("foaming") of cells in culture from a number of mammalian species, including monkeys, cattle, cats, and reportedly in humans. Persistent infection with these viruses is not associated with any known disease.

Recent studies using improved diagnostic assays have shown no evidence of foamy virus infection of humans in studies of large populations (approximately 8,000 persons). Given these results, the identification of seroreactivity in five persons occupationally exposed to non-human primates is notable. The PCR identification of viral genome sequences in biologic specimens from all five, and isolation of the virus from two, confirm virus infection in these workers.

The present invention includes the isolation and characterization of a spumavirus, SFVHu-3, that was shown to have been transmitted from a non-human primate to a human at some point in the past. The retrovirus of the present invention, unlike another retrovirus of a more virulent nature, HIV-1 (Human Immunodeficiency Virus), does not appear to be readily transmitted from human to human. The spumavirus of the present invention can be used in constructing protocols for diagnosing spumavirus infections and may be used as a vector in gene therapy procedures.

The present invention also includes methods and compositions for detecting spumavirus in biological fluids. The methods and compositions, including kits, can be in any configuration well known to those of ordinary skill in the art. The present invention also includes antibodies specific for the spumavirus and antibodies that inhibit the binding of antibodies specific for the spumavirus. These antibodies can be polyclonal antibodies or monoclonal antibodies. The antibodies specific for the spumavirus can be used in diagnostic kits to detect the presence and quantity of spumavirus in biological fluids or in organs from nonhuman primates for xenotransplantation. Antibodies specific for spumavirus may also be administered to a human or animal to passively immunize the human or animal against spumavirus, thereby reducing infection after accidental exposure to nonhuman primate bodily fluids.

The present invention also includes compositions and methods, including kits, for detecting the presence and quantity of antibodies that bind spumavirus in body fluids. The methods, including kits, can be in any configuration well known to those of ordinary skill in the art. Such kits for detection of spumavirus itself or detection of antibodies to the spumavirus can be used to monitor the blood supply for the presence of spumavirus in the blood supply.

The present invention also includes methods and compositions comprising recombinant live virus vaccines. Exogenous genes can be inserted into the genome of the virus of the present invention. The genes can code for any protein for which vaccination or gene therapy is desired. SFVHu-3 can provide a high level of antigen to the host carrying the virus. For example of such use, SFVHu-3 is administered to a human, the virus would infect the cells, replicate and provide antigens to the immune system of the human. A novel aspect of such recombinant live viruses is that SFVHu-3 does not cause disease in the human. Additionally, there is no transmission from one human to another non-infected human, even by close contact with exchange of bodily fluids. The recombinant live virus vaccines of the present invention are a safe way to provide antigen in a most optimum method to the immune system.

The present invention further includes methods and compositions for the use of a replicating viral system to kill live dividing cells in a host or in vitro. In in vitro uses, SFVHu-3 can be used to detect and kill rapidly dividing cells. Foamy viruses, including SFVHu-3, can infect a wide variety of species of cells and can be used in many in vitro cell systems. For example, if the assay of the in vitro cell system required the identification of quiescent cells, application of SFVHu-3 to the tissue culture system would result in the selection of the rapidly dividing cells by SFVHu-3. All of the tissue culture cells would be infected, but only the dividing cells would be destroyed because SFVHu-3 has a productive infection and its cytopathic destruction effects only dividing cells. The remaining non-dividing cells of the culture would remain alive.

In a host, the ability of SFVHu-3 to infect dividing cells provides an excellent treatment for conditions due to the presence of rapidly dividing cells. For example, a person with disease due to rapidly dividing cells, such as cancer or any known angiogenic condition, could be infected with SFVHu-3. Such virus may or may not carry other, exogenous genes for other effects in the host. Because SFVHu-3 does not cause disease in humans and there is no transmission of the virus to close contacts with humans, only the person with the disease due to rapidly dividing cells will be treated. In addition, only the rapidly dividing cells of that person will be infected by SFVHu-3, and the rest of the body will remain uninfected. The virus will infect the rapidly dividing cells and kill them. For example, a person with a fast growing tumor would be infected with SFVHu-3 and the cells of the tumor would be destroyed by the virus. The SFVHu-3 can be recombinantly modified to be selective for cellular receptors on the tumor to make the virus even more specifically targeted to just those cells.

Such treatment with SFVHu-3 could be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels.

Accordingly, it is an object of the present invention to provide a composition comprising a novel spumavirus.

It is another object of the present invention to provide a method of detecting a spumavirus.

It is yet another object of the present invention to provide methods and compositions for detecting the presence and amount of spumavirus in a body fluid or organ.

A further object of the present invention is to provide compositions and methods for treating genetic and physiologic disorders using gene therapy techniques comprising the novel spumavirus of the present invention as a vector for nucleic acid sequences and antisense sequences.

Another object of the present invention is to provide compositions and methods useful for manipulating the expression of genes.

Yet another object of the invention is to provide vaccines.

Yet another object of the present invention is to provide compositions and methods for treating viral infections in humans or animals.

Another object of the present invention is to provide compositions and methods that are effective in treating genetic diseases.

Yet another object of the present invention is to provide a method of treating microbial infections in humans or animals.

It is another object of the present invention to provide for treatments of conditions that are caused in part by rapidly dividing cellular growth.

Another object of the present invention is to provide live recombinant virus vaccines.

An object of the present invention is to provide diagnostic tools such as antibodies or antigens for the monitoring of the blood supply or organ and tissue donation for the presence of spumavirus.

These and other features and advantages of the present invention will become apparent after a review of the following detailed description of the disclosed embodiments and the appended claims.

DETAILED DESCRIPTION OF THE INVENTION

In response to the identification of simian immunodeficiency virus infection in an occupationally exposed workers, Centers for Disease Control and National Institutes for Health collaborated in an anonymous serosurvey of persons with similar work exposures. Simian immunodeficiency virus seroreactivity was present in 3/427 (0.64%) stored serum samples from these anonymous workers (See CDC, Anonymous survey for simian immunodeficiency virus (SIV) seropositivity in SIV laboratory researchers—United States, 1992. MMWR, Morb. Mort. Wkly. Rep. 1992; 41: 814–5; Khabbaz R. F., et al. Brief report: infection of a laboratory worker with simian immunodeficiency virus. New Eng. J. Med. 1994; 330: 172–7). Consequently, a voluntary testing and counseling program was developed that allowed linkage between specific exposures or health outcomes and serostatus of persons occupationally exposed to simian immunodeficiency virus. The workers enrolled in this voluntary, linked, prospective simian immunodeficiency virus surveillance are also at occupational risk for exposure to other retroviruses common in nonhuman primates (non-human primates).

Therefore, in 1995, the linked surveillance was expanded to include voluntary testing and counseling for exposure to simian spumaviruses (more commonly called simian foamy viruses, or SFV), simian T-lymphotropic viruses (STLV), and simian type D retroviruses (STRV). 1,823 samples from 13 institutions in the United States had been tested for simian immunodeficiency virus; samples from 231 of the participating volunteer workers were also tested for other retroviruses from non-human primates. Three of these 231 workers (1.3%) were determined to be infected with a SFV-like virus by serology and PCR.

An immunofluorescent assay that was developed using cells infected with SFV serotype 3 identified antibodies to a SFV-like virus in recently collected serum specimens from all three workers. The 3 specimens were also western blot positive, showing reactivity to both p70 and p74 gag precursor bands of SFV-3 antigen. Repeat testing of additional sera obtained from these 3 workers at later time points are also positive in both assays. (These workers or cases are herein identified individually as Case A, Case B, and Case C.)

Figure 5:
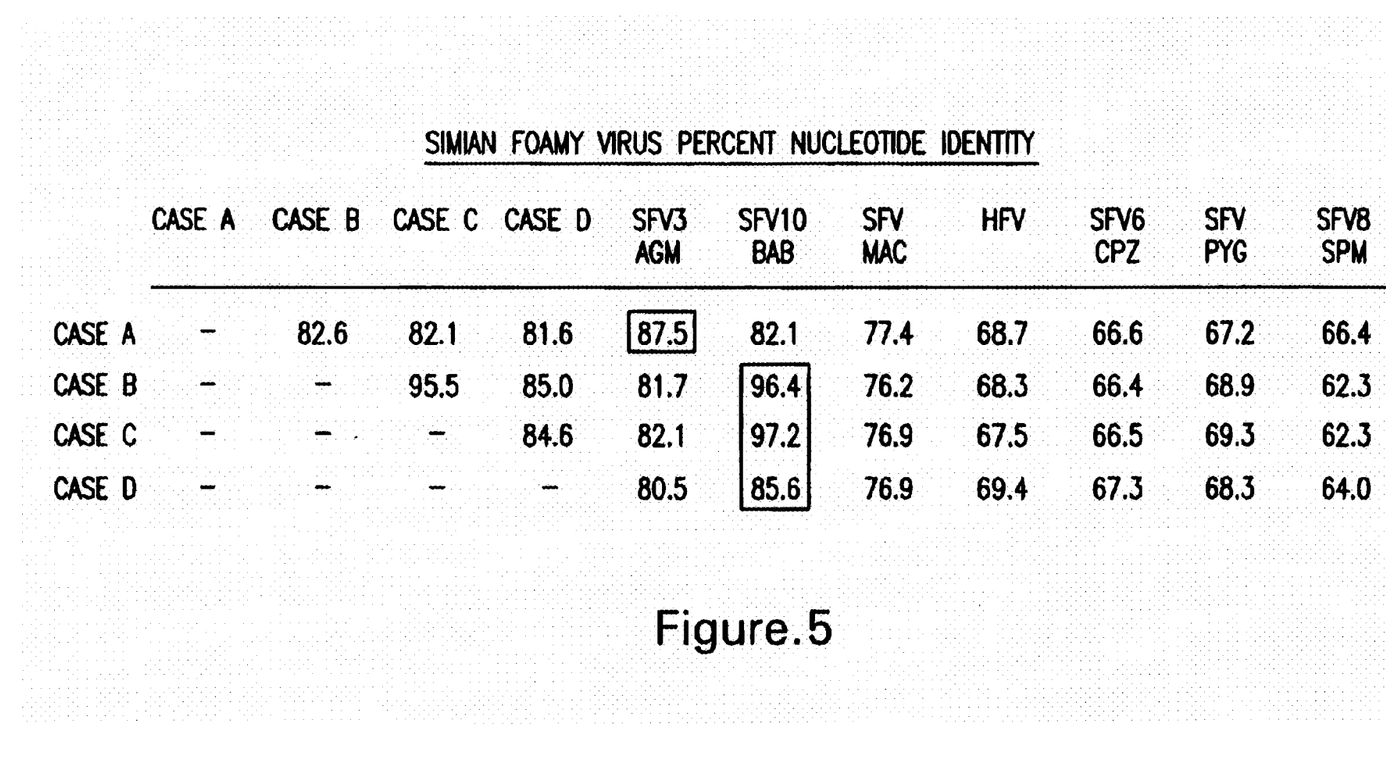
FIG. 5 is a comparison of the nucleotide homology of the sequenced portion of the present invention and other spumaviruses.
Figure 6:
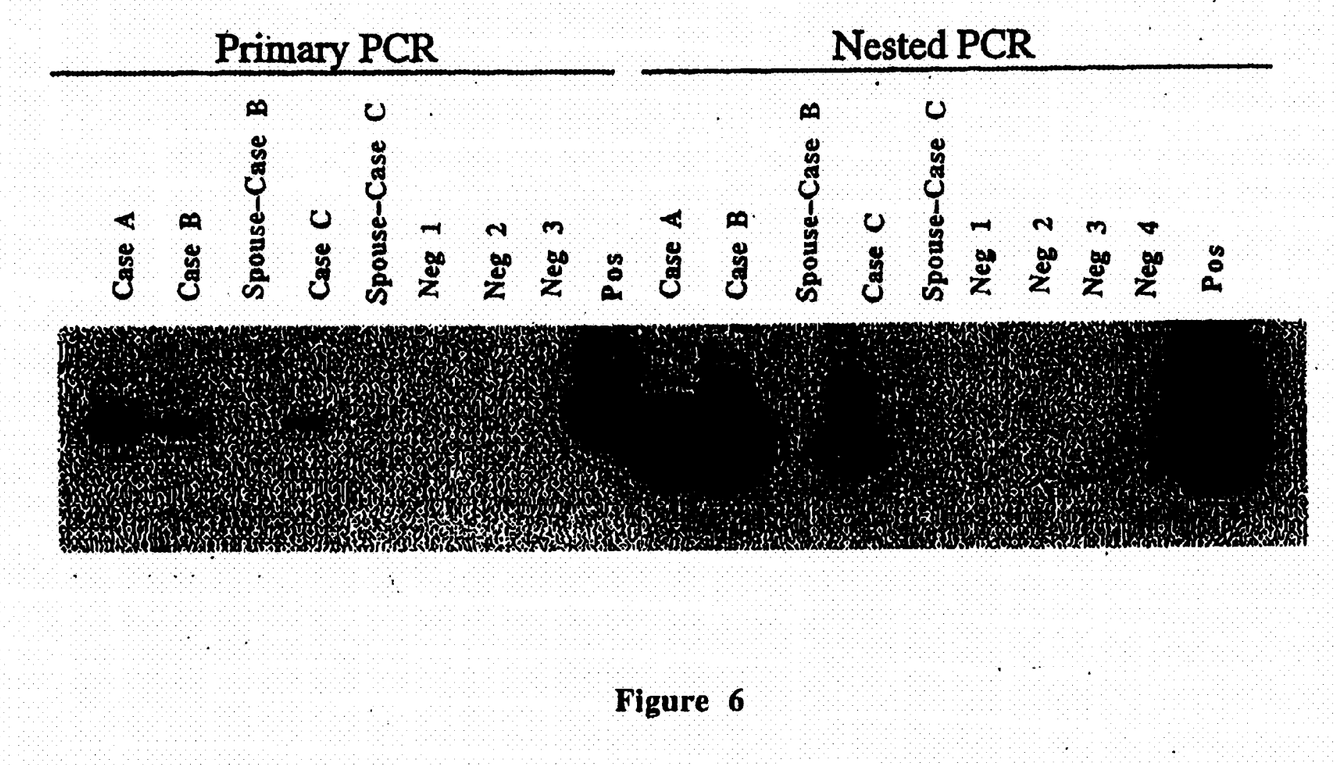
FIG. 6 shows the PCR analysis of peripheral blood lymphocytes of a 153-bp FV pol sequence.

Additional blood samples from these three cases were tested for SFV proviral DNA sequences using polymerase chain reaction (PCR) assays employing primer sets from two regions of the polymerase gene that are conserved among known primate foamy viruses. AU three cases were PCR positive in both regions. The PCR products from one region were sequenced. The sequences from each case were distinct from each other. FIG. 5 shows that there was 62–94% homology to known non-human primate foamy virus sequences. The partial sequences, produced with DNA polymerase PCR primer, of the viral sequence of the present invention is shown below. Seq. ID 1 is a viral DNA sequence isolated from isolated from PBLs from Case C and Seq. ID 2 is a viral DNA sequence infected Mus dunni cells. There is 99.53% sequence identity between the two sequences. This near sequence identity confirms that the virus originated from Case C. The corresponding RNA sequences and resulting proteins can be deduced from these sequences.

Figure 4:
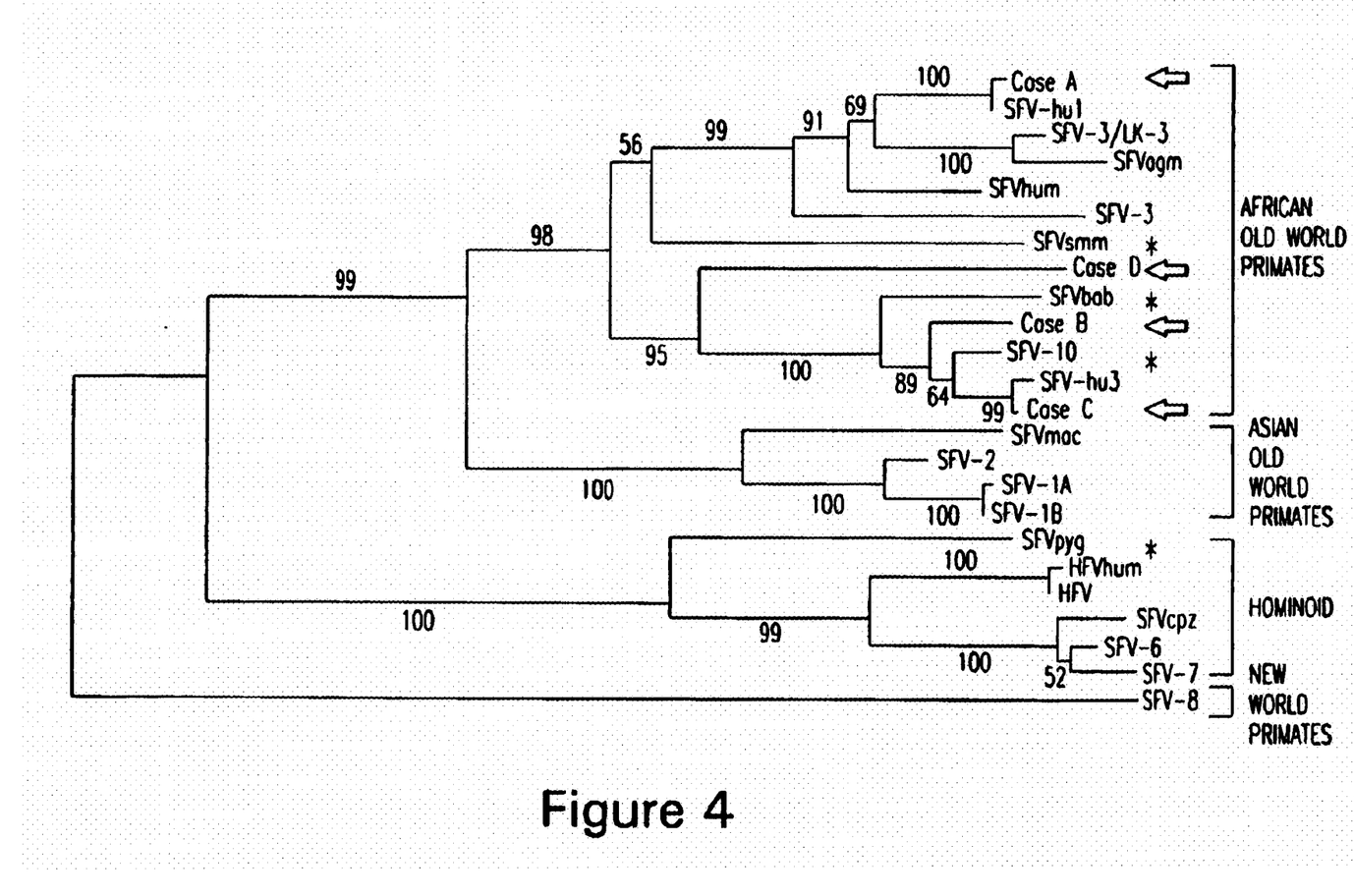
FIG. 4 is a phylogenetic tree showing the relationships between the sequences of the viruses of the novel spumavirus of the present invention and known spumaviruses.

Seq. ID 1
    AATTACTACA AGGACAATAT CCAAAAGGTT
    ACCCAAAACA TTATAGCTAT AAATTACAAG
    AAGGTCATGT TGTTGTAGAA CGACCTAATG
    GCATTAGGAT TATTCCTCCT AAAGCTGATC
    GTTCTACTAT TATTCTACAA GCACATAATA
    TTGCTCATAC AGGAAGAGAC TCGACATTCT
    TAAAGGTCAC TTCCAAGTAT TGGTGGCCAA
    ATCTTAGAAA GGATGTGGTT AAAGTCATAA
    GACAATGTAA ACAGTGTCTG GTGACTAACC
    AAGCTGTTTT AACAGCGCCT CCAATACTTA
    GGCCTGAGAG GCCTTTAAAG CCTTTTGATA
    AATTTTATAT TGATTATATT GGGCCTTTAC
    CTCCTTCAGG AGGATATTTA CATGTCCTTG
    TAGTGGTCGA TGGTATGACT GGATTTGTTT
    GGTTA Seq. ID 2
    ATTACTACAA GGACAGTATC CAAAAGGTTA
    CCCAAAACAT TATAGCTATA
    AATTACAAGA AGGTCATGTT GTTGTAGAAC
    GACCTAATGG CATTAGGATT
    ATTCCTCCTA AAGCTGATCG TTCTACTATT
    ATTCTACAAG CACATAATAT
    TGCTCATACA GGAAGAGACT CGACATTCTT
    AAAGGTCACT TCCAAGTATT
    GGTGGCCAAA TCTTAGAAAG GATGTGGTTA
    AAGTCATAAG ACAATGTAAA
    CAGTGTCAGG TGACTAACCA AGCTGTTTTA
    ACAGCGCCTC CAATACTTAG
    GCCTGAGAGG CCTTTAAAGC CTTTTGATAA
    ATTTTATATT GATTATATTG
    GGCCTTTACC TCCTTCAGGA GGATATTTAC
    ATGTCCTTGT AGTGGTCGAT
    GGTATGACTG GATTTGTTTG GTTA The relationship between each of the isolates and other known spumaviruses is shown in FIG. 4 which is a phylogenetic tree showing the percent homology of the nucleotide sequences of these viruses and in FIG. 5.

Seq. IDs 1 and 2 can be used for all the molecular biological techniques known to those skilled in the art. Such uses include, but are not limited to, generation of probes and vectors containing the sequences, antisense sequences derived from such sequences, and proteins synthesized using the sequences. RNA and other nucleic acid derivatives are contemplated by the present invention. The FV proviral pol sequence In foamy viruses, the LTR aids in the replication of the virus. The LTR is transactivated by a virus-specific protein, and unlike a related retrovirus, HIV (Human Immunodeficiency Virus), no human cellular transcription factors activate the virus. LTRs in retroviruses like HIV have conserved consensus sequences for cellular transcription factors.

It is known that another human-derived spumavirus has stable, conserved LTRs and internal promoters, providing conserved transcriptionally important regions in such viruses. For gene therapy uses, this stability is very important. This indicates that the virus is not acquiring human sequences that would cause it to possibly become virulent or at least cause disease in humans due to introduced mutations. With such conserved regions, SFV-Hu3, would be an excellent vector, vaccine or gene therapy agent for humans. This stability is surprising in light of the high instability of the LTR of the virus known as HFV, Human Foamy Virus. HFV was derived from a nasocarcinoma and is now believed not to be a human foamy virus, but a chimpanzee virus. The HFV LTR is unstable and has lots of deletions, thus making it an undesirable vector.

The foamy viruses are unique in that at the 3' end of the env gene there is an internal promoter, IP. ORF 1 codes for a transactivator protein, TAF. TAF activates IP. Once the virus infects the cell, a little TAF is made, this TAF activates the internal promoter IP, which then causes the virus to make lots of TAF. Once sufficient quantity of TAF is made, the TAF functions to initiate the promoter found in the 5' LTR.

SFVHu-3 is found in the peripheral blood lymphocytes (PBL) of the host and is cultured from such cells in tissue culture systems.

Virus isolation of SFVHu-3 was accomplished by co-culturing the PBLs (peripheral blood lymphocytes) of the person identified as Case C with Mus dunni cells. Importantly, this isolation has identified a cell line that is a susceptible host cell line for isolating SFVHu-3 and other baboon-like spumaviruses. Reverse transcriptase activity was detected in co-cultures from the cells exposed to Case C PBLs but not from controls. Transfer of supernatant from the above cells exposed to Case C's PBLs passed this reverse transcriptase activity to uninfected cells, which subsequently showed cytopathic effect (CPE). This finding indicated that the infectious agent in Case C's PBLs was transmitted to tissue culture cells which were used to transfer the infectious agent into other tissue culture cells. Additionally, this indicated that the infectious agent reproduced in the Mus dunni cells. DNA-PCR of infected cells was found to be positive for a SFV-like virus. Infected cells showed strong reactivity with all 3 cases' sera by both immunofluorescent assay and western blot and no reactivity with normal sera controls. By electron microscopy, infected Mus dunni cells, derived from cell free supernatants from cells infected by exposure to infected PBLs, showed a morphology characteristic of foamy virus infection (See FIG. 1).

The present invention is directed to compositions and methods comprising a new spumavirus, SFVHu-3. The virus was isolated from a human who had worked with nonhuman primates. The new spumavirus, or foamy virus, does not appear to cause any disease in the human hosts. The new virus of the present invention can be used an excellent vector for gene therapy and for vaccination purposes. Additionally, the antibodies or other detection methods for detecting the new virus can be used important in detecting the presence of this and related viruses for xenotransplantation. In addition, the novel spumavirus of the present invention can be used as a reagent in pathogenicity studies of these and related viruses. Moreover, the sequences of the novel spumavirus of the present invention can be used as probes to detect virus in biological samples. Vectors include but are not limited to procaryotic, eucaryotic and viral vectors.

Many new and potentially useful technologies are being developed which use viral vectors and may form the basis of future medical cures and therapies. Examples of such technologies include, but are not limited to, gene replacement, antisense gene therapy, in situ drug delivery, treatment of cancer or infectious agents, and vaccine therapy. However, to be successful, these technologies require an effective means for the delivery of the genetic information across cellular membranes. SFVHu-3 can function as a vector to carry such genes when infecting cells.

The recent advent of technology, and advances in the understanding of the structure and function of many genes makes it possible to selectively turn off or modify the activity of a given gene. Alteration of gene activity can be accomplished many ways. For example, oligonucleotides that are complementary to certain gene messages or viral sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion gene activity can be modulated.

The ability to deactivate specific genes provides great therapeutic benefits. For example, it is theoretically possible to fight viral diseases with antisense molecules that seek out and destroy viral gene products. In tissue culture, antisense oligonucleotides have inhibited infections by herpesviruses, influenza viruses and the human immunodeficiency virus that causes AIDS. It may also be possible to target antisense oligonucleotides against mutated oncogenes. Antisense technology also holds the potential for regulating growth and development. However, in order for the gene therapy to work, antisense sequences must be delivered across cellular plasma membranes to the cytosol.

Gene activity is also modified using sense DNA in a technique known as gene therapy. Defective genes are replaced or supplemented by the administration of "good" or normal genes that are not subject to the defect. Instead of being defective, the gene have been deleted, thus replacement therapy would provide a copy of the gene for use by the cell. The administered normal genes can either insert into a chromosome or may be present as extracellular DNA and can be used to produce normal RNA, leading to production of the normal gene product. In this fashion gene defects and deficiencies in the production of a gene product may be corrected.

Still further gene therapy has the potential to augment the normal genetic complement of a cell. For example, it has been proposed that one way to combat HIV is to introduce into an infected person's T cells a gene that makes the cells resistant to HIV infection. This form of gene therapy is sometimes called "intracellular immunization." Genetic material such as a polynucleotide sequence may be administered to a mammal in a viral vector to elicit an immune response against the gene product of the administered nucleic acid sequence. Such gene vaccines elicit an immune response in the following manner. First, the viral vector containing the nucleic acid sequence is administered to a human or animal. Next, the administered sequence is expressed to form a gene product within the human or animal. The gene product inside the human or animal is recognized as foreign material and the immune system of the human or animal mounts an immunological response against the gene product. The virus of the present invention may be used as a viral vector to provide the foreign nucleic acid sequences to the intracellular metabolic processes.

Additionally, gene therapy may be used as a method of delivering drugs in vivo. For example, if genes that code for therapeutic compounds can be delivered to endothelial cells, the gene products would have facilitated access to the blood stream. Additionally, cells could be infected with a retroviral vector such as the present invention carrying nucleic acid sequences coding for pharmaceutical agents that prevent infection from occurring in the retrovirally infected cells.

The novel spumavirus of the present invention can also be used a safe and effective vaccine agent. Genetic sequences for immunogenic proteins from a variety of infectious agents can be incorporated into the foamy virus RNA. Once inside a cell, the gene product is expressed and releases the immunizing peptide to the body's immune system. In another method, the virus of the present invention can be used to immunize the body against cell markers found on cancer or tumor cells. The genetic sequence of the cancer cell marker is incorporated into the foamy virus RNA and after infection with the virus, the expressed gene product stimulates the immune system. The patient's immune system is used to remove the cancerous cells, obviating the need for chemotherapeutic methods.

The DNA sequences of the virus of the present invention can be used in a variety of methods, including, but not limited to, PCR assays. Additionally, the sequences can be used to easily detect the presence of baboon-like spumaviruses, similar to SFVHu-3, in xenotransplantation of organs, tissues or cells. For example, before a baboon heart is given to a human recipient, the baboon or heart tissue can be test for the presence of spumaviruses. Additionally, after xenotransplantation of the baboon heart into the human, the human can be monitored for the presence of the virus. The sequences can also be used to test for transmission of spumaviruses in animals who are in contact with nonhuman primates. For example, animal care workers in nonhuman primate centers can be tested routinely for exposure to spumaviruses and for the transmission of viruses from the animals cared for to the caretaker.

The antibodies of the present invention can be used to detect the presence of the virus or viral particles of the present invention. These antibodies can be used in diagnostic or screening kits to assess the presence of the virus, for example, in clinical specimens. Additionally, the antibodies can be used to screen organs from nonhuman primates that may be used in humans. Detection of the presence of a virus that is transmitted from nonhuman primates to humans would be crucial in providing virus-free organs for transplantation.

The virus of the present invention can be used for the treatment of conditions due to the presence of rapidly dividing cells. In a host, the ability of SFVHu-3 to productively infect dividing cells provides an excellent treatment for conditions due to the presence of rapidly dividing cells. For example, a person with disease due to rapidly dividing cells, including but limited to cancer or any known angiogenic condition, could be infected with SFVHu-3. Such virus may or may not carry other, exogenous genes for other effects in the host. Because SFVHu-3 does not cause disease in the host and there is no transmission of the virus to contacts with the host, only the person with the condition due to rapidly dividing cells will be treated. In addition, only the rapidly dividing cells of that host person will be productively infected by SFVHu-3. Other cells in the body may be infected but will not be killed because the infection in nondividing cells is not productive. The virus will productively infect the rapidly dividing cells and kill them. For example, a person with a fast growing tumor would be infected with SFVHu-3 and the cells of the tumor would be destroyed by the virus. Additionally, the virus may be given to a person prior to the person developing a condition caused by dividing cells, and when the cells begin dividing, the virus would then undergo a productive infection and kill the cells. This therapy may halt or inhibit such conditions as leukemia or angiogenesis dependent diseases such as macular degeneration.

Such treatment with SFVHu-3 could be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels.

Another such condition is cancer or tumor growth. Cancer or tumors include both solid tumors and other types. Infection with the virus of the present invention, which causes no disease and does not effect the host systemically, is an improvement over currently known treatments that involved systemically administered agents. Such chemotherapeutic agents kill rapidly dividing cells but also cause trauma to the entire person. The dosages of such chemotherapeutic agents must be titered between killing the cancer and killing the patient.

In contrast, treatments of cancer with the present invention are not as harmful to the patient. The virus can either be administered systemically or injected in situ into the tumor. The virus will only replicate in rapidly dividing cells and will not effect cells that are not dividing. The infected cells are killed and tumor growth is stopped. The virus may be administered in one treatment or in a series of treatments.

The SFVHu-3 of the present invention can be recombinantly modified to be selective for cellular receptors on the tumor to make the virus even more specifically targeted to just those cells. Additionally, the virus may have altered promoter regions that can be selectively activated to cause a productive infection. The combination of different levels of control of the virus, both natural and recombinantly produced, are contemplated in the present invention. A virus could be made specific for attachment to only certain types of cellular receptors, for those cells that are dividing, and will only undergo replication if another exogenous promoter factor is present. Viral infection by two or more individually defective viruses, that require factors or promoters supplied by other foamy viruses or any type of virus, could provide for many levels of control of infection or treatment of specific conditions.

The virus may be administered to the host, for cancer treatment, gene therapy or vaccination by any methods known to those skilled in the art. Such methods include but are not limited to injection, inhalation, ingestion, topical administration and implantation. The virus may be killed or live, depending on the treatment considered.

The inventors of the present invention believe that the virus of the present invention, comprising the isolate from Cases C, SFVHu-3 is a definitive isolation of an SFV-3-like spumavirus from a person exposed to nonhuman primates. The virus does not appear to cause disease and does not appear not transmitted to close household contacts or sexual contacts. This belief is supported by the epidemiology data, the PCR and sequencing data and the serology data.

The isolate from Case C, SFVHu-3, was deposited with the ATCC, under the Budapest Treaty on Apr. 8, 1998, and was assigned ATCC No. VR-2602.

The present invention is further described by the examples which follow. Such examples, however, are not to be construed as limiting in any way either the spirit or scope of the present invention. In the examples, all parts are parts by weight unless stated otherwise.

EXAMPLE 1

Case C is an animal handler who has worked with non-human primates for more than 3 decades. Case C recalls multiple minor injuries and mucocutaneous exposures to non-human primate blood, body fluids, or unfixed tissues. Case C reported a severe baboon bite around 1980. Case C is in good health. Case C has been in a monogamous sexual relationship for nearly three decades, during which barrier methods of contraception have not been employed and spermicides were used for no more than a 6 month period. Case C's spouse is negative for SFV-like infection by both serologic and PCR testing. Retrospective analysis of sera archived from Case C in 1988 showed the sera to have antibodies to SFV. See FIG. 3, lane 8 is Case C's sera from 1988, and lane 11 is sera from the spouse of Case C.

Figure 3:
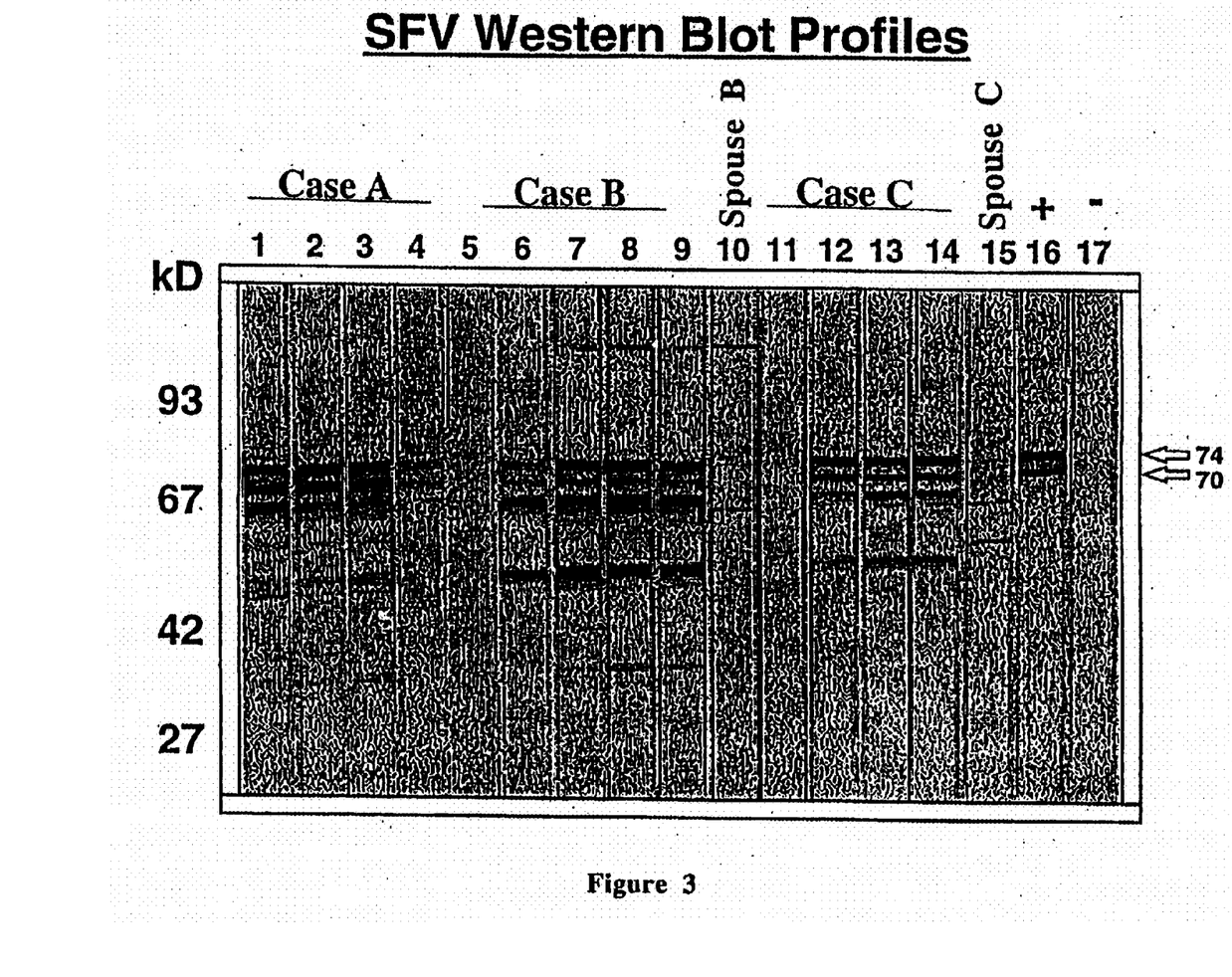
FIG. 3 is a Western blot of sera from Case A (infected with SFVHu-1), Case B and Case C (infected with SFVHu-3) and the sera of spouses of two of the cases. The sera was tested against the whole cell lysate from Cf2Th cells infected with the spumavirus, SFV-3. Whole cell lysate of uninfected Cf2Th were used as a control for seroreactivity towards nonviral proteins. In addition, the sera of Case B provides a view of the history of infection because of the existence of Case B sera obtained in 1967, and in 1978, 1980, and 1981.

The western blot of FIG. 3 shows whole cell lysate from Cf2Th cells infected with SFV-3 and each individual lane with different antisera. In FIG. 3, particular viral proteins that show infection are the proteins with molecular weight of approximately 70–80 Daltons (p70 gag protein) and the proteins at approximately 130–140 Daltons (an envelope protein). The western blot of FIG. 3 shows whole cell lysate from Cf2Th cells infected with a spumavirus. These proteins are not detectable in the western blot of FIG. 3 by normal sera, (lane 1) but are detectable by antisera from Case C.

EXAMPLE 2

Peripheral blood lymphocytes (PBLs) were isolated from Case C and were cultured with IL-2 for 48 hours, in RPI media with 10% fetal Calf serum, and penn-strep antibiotics. After 48 hours, the PBLs were added to the Mus dunni cells and co-cultured for 2–4 weeks. The cells were in DMEM supplemented with 2% nonessential amino acids, 20% fetal calf serum, and pen-strep antibiotics. 1 mL supernatants were collected from the cell cultures every 3 to 4 days and tested for reverse transcriptase. Procedures for PBL treatment, culturing of Mus dunni cells and reverse transcriptase activity were procedures known to those in the art. For example, see Heneine, W., et al. "Detection of reverse transcriptase by a highly sensitive assay in sera from persons infected with HIV-1." (1995). J. Infectious Diseases, 171:1201–6.

EXAMPLE 3

Because of the positive reverse transcriptase activity from cells from Case C, peripheral blood lymphocytes from Case C were cultured with IL-2 for 48 hours prior to addition to Mus dunni cells, human lung fibroblasts, and normal human peripheral blood lymphocytes. Supernatants were collected every 3 to 4 days and tested for reverse transcriptase activity. Each time the 1 mL sample of supernatant was taken for reverse transcriptase activity, a 5 mL sample of supernatant was taken and frozen at $-80\,°$ C. in order to preserve a sample of the virus producing the reverse transcriptase activity.

Figure 2:
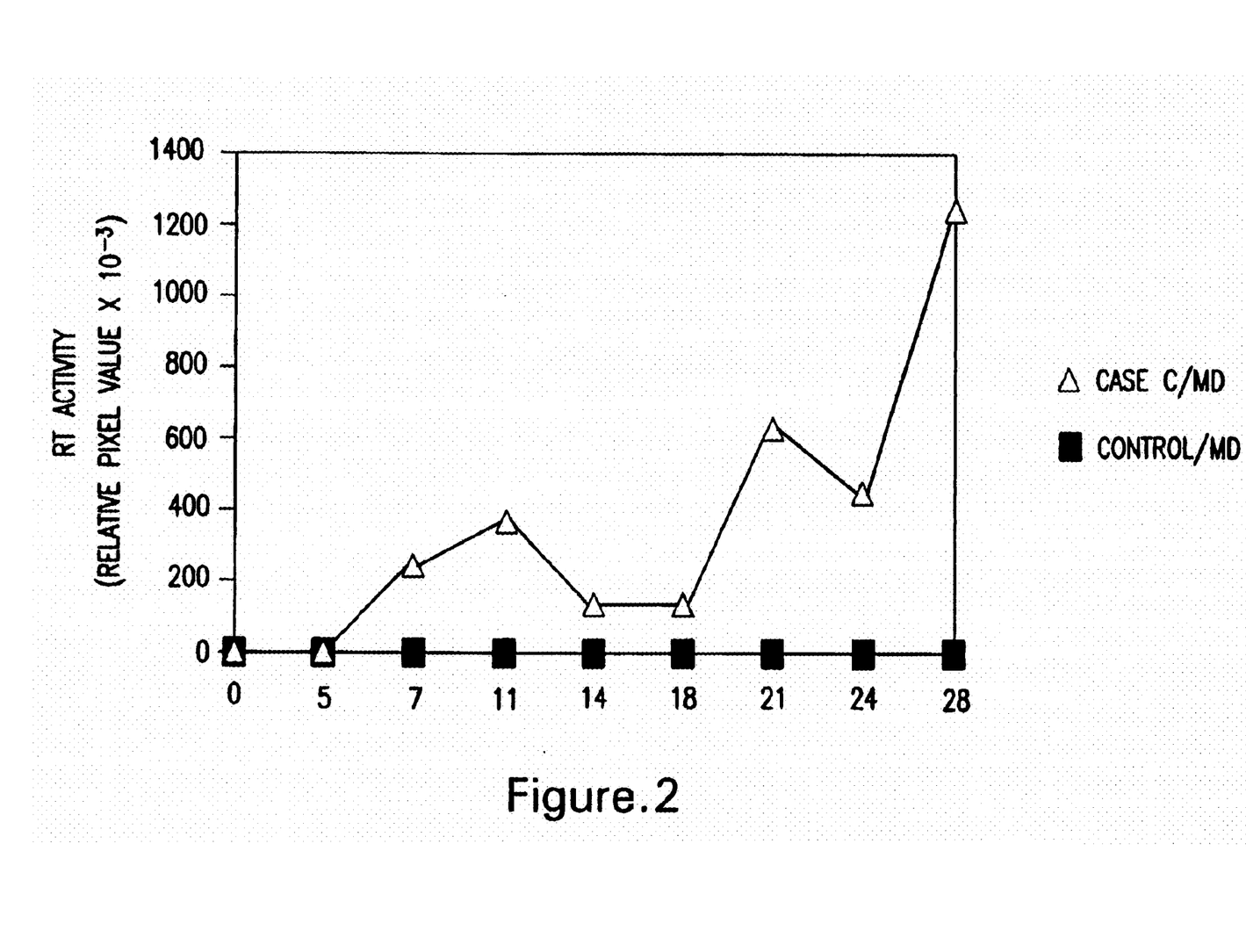
FIG. 2 shows tissue culture reverse transcriptase activity in Mus dunni cells co-cultured with peripheral blood lymphocytes from an infected case worker. Along the baseline is another line showing control Mus dunni cells that were co-cultured with normal human peripheral blood lymphocytes, indicating there was no constitutive reverse transcriptase activity in these cultures.

At day 7, reverse transcriptase testing showed a slightly positive signal in the Mus dunni cell culture. The reverse transcriptase activity increased over time. (See FIG. 2).

The activity in control Cf2Th cells that were treated as above, except for exposure to normal PBLs instead of infected PBLs, was shown by the lower line that overlaps the baseline. There was no reverse transcriptase activity inherently in these Mus dunni cells, providing evidence that there was no contamination by a retrovirus or spumavirus by the tissue culture cells.

EXAMPLE 4

Figure 1:
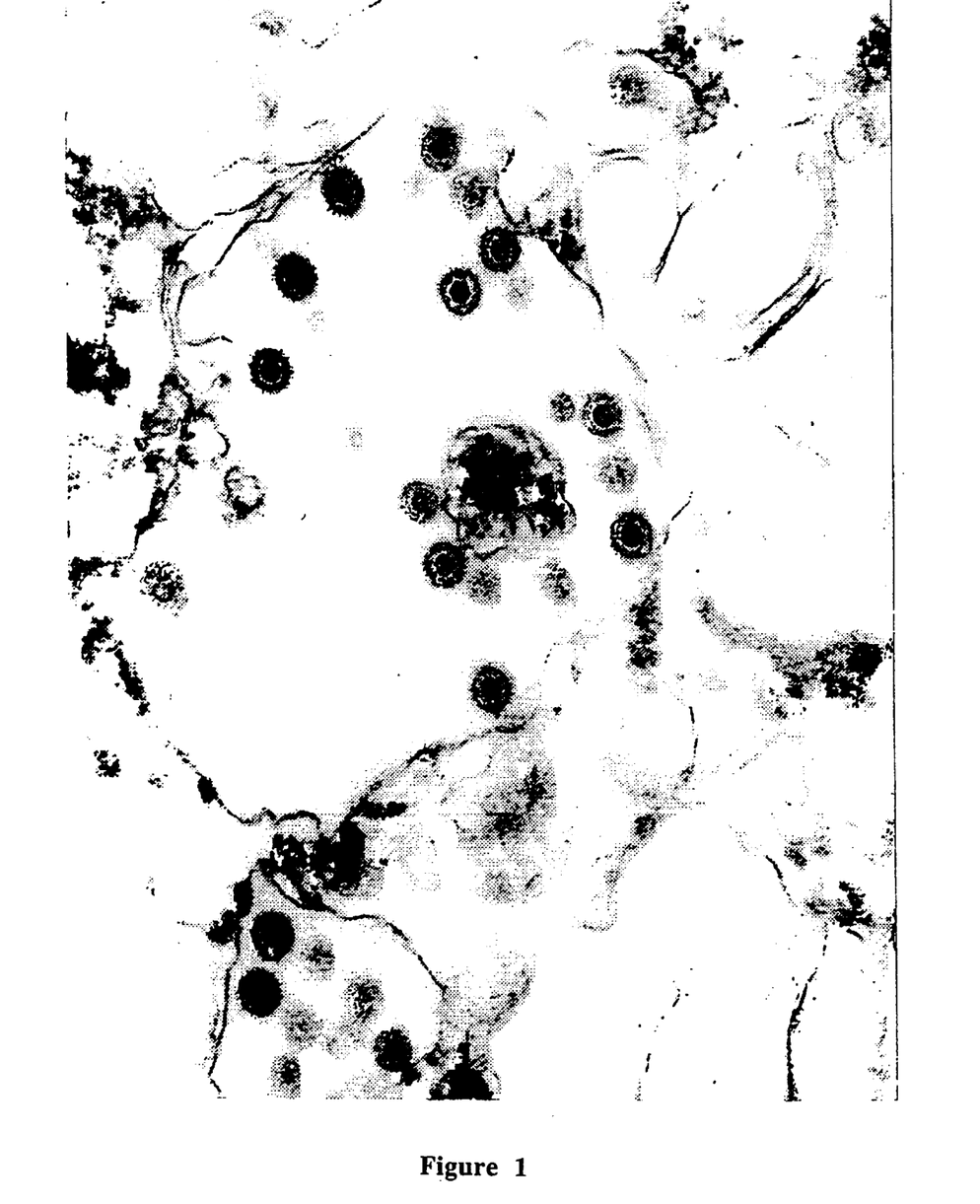
FIG. 1 shows a transmission electron microscope photomicrograph of SFVHu-3 viral particles in Mus dunni cells.

At the peak of reverse transcriptase activity as described in Example 2, cell-free supernatants were transferred to fresh Mus dunni cells growing at $2 \times 10^5$ cells/mL. At day 4 in the new culture, cytopathic effects and syncytia was observed. Transmission electron microscopy showed viral particles in and around the cells (See FIG. 1). Viral particles were isolated from these cultures and were stored at the Centers for Disease Control and were deposited at the ATCC.

The Mus dunni cells were obtained from the American Type Culture Collection (Rockville, Md.).

Having thus described the invention, numerous changes and modifications thereof will be readily apparent to those having ordinary skill in the art, without departing from the spirit or scope of the invention.

What is claimed is:

1. An isolated spumavirus, wherein the spumavirus is infectious to humans, and wherein the spumavirus is deposited with the ATCC under ATCC Deposit No. VR-2602.

2. An isolated spumavirus, wherein the spumavirus is infectious to humans, and wherein the spumavirus comprises the nucleic acid sequence of SEQ ID NO:1.

3. An isolated spumavirus, wherein the spumavirus is infectious to humans, and wherein the spumavirus comprises the nucleic acid sequence of SEQ ID NO:2.

* * * * *

SEQUENCE LISTING

<160> NUMBER OF SEQ ID NOS: 2

<210> SEQ ID NO 1
<211> LENGTH: 425
<212> TYPE: DNA
<213> ORGANISM: Simian Foamy Virus Hu-3

<400> SEQUENCE: 1

```
aattactaca aggacaatat ccaaaaggtt acccaaaaca ttatagctat aaattacaag      60
aaggtcatgt tgttgtagaa cgacctaatg gcattaggat tattcctcct aaagctgatc     120
gttctactat tattctacaa gcacataata ttgctcatac aggaagagac tcgacattct     180
taaaggtcac ttccaagtat tggtggccaa atcttagaaa ggatgtggtt aaagtcataa     240
gacaatgtaa acagtgtctg gtgactaacc aagctgtttt aacagcgcct ccaatactta     300
ggcctgagag gcctttaaag ccttttgata aattttatat tgattatatt gggcctttac     360
ctccttcagg aggatattta catgtccttg tagtggtcga tggtatgact ggatttgttt     420
ggtta                                                                 425
```

<210> SEQ ID NO 2
<211> LENGTH: 424
<212> TYPE: DNA
<213> ORGANISM: Simian Foamy Virus Hu-3

<400> SEQUENCE: 2

```
attactacaa ggacagtatc caaaaggtta cccaaaacat tatagctata aattacaaga      60
aggtcatgtt gttgtagaac gacctaatgg cattaggatt attcctccta aagctgatcg     120
ttctactatt attctacaag cacataatat tgctcataca ggaagagact cgacattctt     180
aaaggtcact tccaagtatt ggtggccaaa tcttagaaag gatgtggtta aagtcataag     240
acaatgtaaa cagtgtcagg tgactaacca agctgtttta acagcgcctc caatacttag     300
gcctgagagg cctttaaagc cttttgataa attttatatt gattatattg gcctttacc     360
tccttcagga ggatatttac atgtccttgt agtggtcgat ggtatgactg gatttgtttg     420
gtta                                                                  424
```